United States Patent [19]

Marshall

[11] Patent Number: 5,293,532
[45] Date of Patent: Mar. 8, 1994

[54] DEVICE AND METHOD FOR POSITIONING AND RELAXING ACCOMMODATION OF THE EYE

[76] Inventor: Forrest A. Marshall, 615 Acadamy Ave., Dublin, Ga. 31021

[21] Appl. No.: 998,258

[22] Filed: Dec. 31, 1992

Related U.S. Application Data

[63] Continuation of Ser. No. 728,543, Jul. 11, 1991, abandoned, which is a continuation-in-part of Ser. No. 642,299, Jan. 17, 1991, Pat. No. 5,046,257, which is a continuation-in-part of Ser. No. 467,269, Jan. 19, 1990, Pat. No. 5,036,592.

[51] Int. Cl.$^5$ .............................................. A61B 3/02
[52] U.S. Cl. ................................... 351/225; 351/222; 351/224; 351/246
[58] Field of Search ............... 351/214, 222, 224, 225, 351/226, 246, 221

[56] References Cited

U.S. PATENT DOCUMENTS

| | | |
|---|---|---|
| 3,843,240 | 10/1974 | Cornsweet . |
| 4,169,664 | 10/1979 | Bailey, Jr. . |
| 4,533,221 | 8/1985 | Trachtman . |
| 4,660,945 | 4/1987 | Trachtman . |
| 4,685,784 | 8/1987 | Kirchhuebel . |
| 4,871,247 | 10/1989 | Haynes . |
| 4,998,820 | 3/1991 | Salibello et al. . |

OTHER PUBLICATIONS

A brochure for R. H. Burton Company 1000 Slit Lamp Special, ©1989, 3 pages.
A brochure for Teknar Ophthasonic A-Scan/B-Scan III (©1990) (2 pages).
A brochure for R. H. Burton Company "Burton" ™ Slit Lamp Packages (4 pages)–no date available.
A brochure for Coherent Novus 2000© Argn Laser System (3 pages)–no date available.
A brochure for Keeler entitled "Focus on Keeler for Indirect Ophthalmoscopy" (4 pages)–no date available.
A portion of a catalog for Keeler Henson CFA 3000 (1 page) no date available.
A portion of a catalog for Keeler Low Vision Aids (undated) (1 page) no date available.
A brochure for Keeler Microlase (undated) (3 pages) no date available.
A catalog for Lombart Instrument (12 pages) no date available.
A catalog for Marco Slit Lamps (undated) (4 pages) no date available.
A brochure for Mentor entitled "Mentor Binocular Indirect Ophthalmoscopes" (3 pages) no date available.
A brochure for Topcon Slit Lamp SL-3D (undated) (2 pages) no date available.
A brochure for Topcon Photo Slit Lamp SL-5D (undated) (6 pages) no date available.
A brochure for Video 2000 slit Lamp (undated) (1 page) no date available.

*Primary Examiner*—Bruce Y. Arnold
*Assistant Examiner*—Hung Xuan Dang
*Attorney, Agent, or Firm*—Kilpatrick & Cody

[57] ABSTRACT

Apparatus and methods for relaxing accommodation of an eye undergoing examination or other optical or medical procedures while concurrently permitting and facilitating positioning of the subject eye. A patch, cover, or other device designed to occlude and visually stimulate the eye opposite the subject eye includes multiple light sources facing the occluded eye. The practitioner illuminates a selected one (or ones) of the light sources within the patch and directs the patient to fixate on the source. As the occluded eye moves to fixate on the illuminated source, the subject eye follows the movement, thereby repositioning itself. Occluding the eye causes the image seen by it to appear to be at infinity, rather than nearby, causing the ocular muscles of both eyes to relax. The availability of multiple light sources within the patch allows the practitioner to reposition the illuminated source relative to the eye without physically moving a wand or otherwise engaging in trial-and-error techniques requiring interruption of the examination or procedure and consequent loss of concentration.

13 Claims, 3 Drawing Sheets

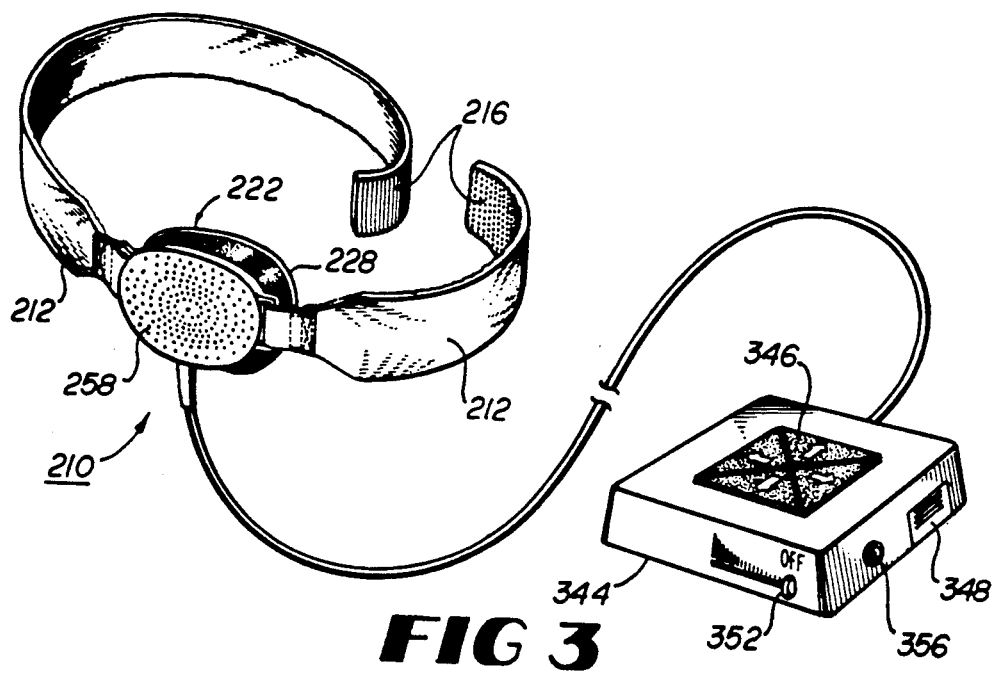
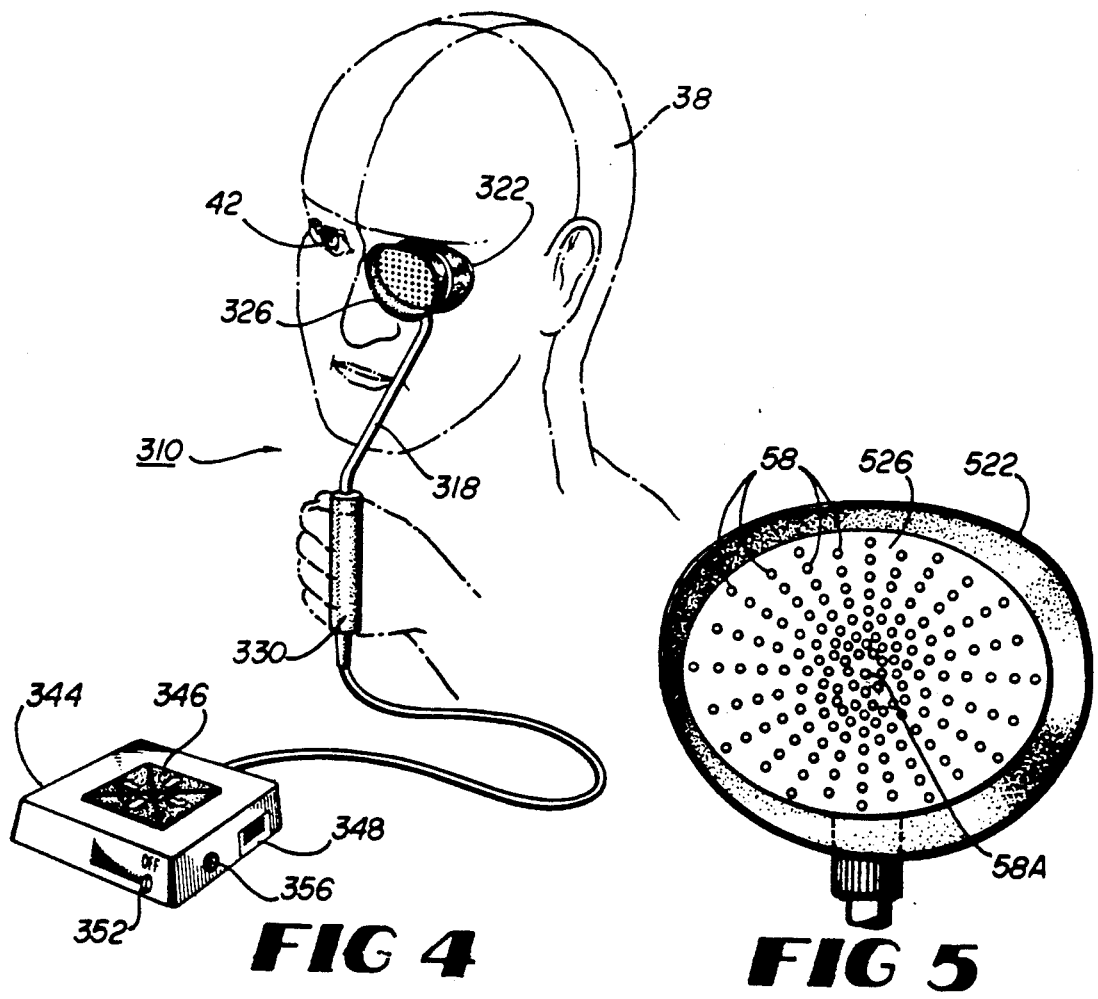

DEVICE AND METHOD FOR POSITIONING AND RELAXING ACCOMMODATION OF THE EYE

This application is a continuation of application Ser. No. 07/728,543, filed Jul. 11, 1991, having the same title, now abandoned, which copending application is a continuation-in-part of application Ser. No. 07/642,299 (now U.S. Pat. No. 5,046,257) filed Jan. 17, 1991, entitled "Determining and Marking Apparatus and Method for Use in Optometry and Ophthalmology," which application was a continuation-in-part of application Ser. No. 07/467,269 (now U.S. Pat. No. 5,036,592) filed Jan. 19, 1990, entitled "Determining and Marking Apparatus and Method for Use in Optometry and Ophthalmology," each of which applications is incorporated herein in its entirety by this reference.

FIELD OF THE INVENTION

This invention relates to apparatus and techniques for positioning and relaxing accommodation of a subject eye by occluding and visually stimulating the eye opposite the subject eye.

BACKGROUND OF THE INVENTION

Accommodation, or the adjustment made by the eye for seeing at different distances, is often characterized by convergence and ocular muscle fatigue when a patient attempts to focus a sharp image—particularly one near to the eye—on the eye's retina for more than a minimal period of time. Such ocular fatigue typically may be uncomfortable for the patient, making examinations and procedures performed during the period less pleasant for the patient and, consequently, for the practitioner as well. Existence of accommodation and convergence also may corrupt measurements made during various ocular examinations, potentially rendering eyeglass lens prescriptions inaccurate. Because a patient may tend to reposition a subject eye (or allow it to wander) as the ocular muscles tire, accommodation also may affect ophthalmic and medical procedures, including modern laser surgeries and retinal photography, which require that the subject eye remain stationary for relatively long periods.

A variety of means to counteract accommodation of the eye have thus been developed or suggested. Paralytic drugs, for example, may be used to immobilize the muscles controlling the lens of an eye and render it motionless when necessary or desired. The technique of "fogging," or placing a predetermined sequence of lenses before a subject eye, additionally may be used to relax accommodation of the eye when using autorefractometers or similar instruments to determine the appropriate corrective lenses for a particular patient. Cornsweet U.S. Pat. No. 3,843,240, incorporated herein in its entirety by this reference, discloses an alternative method for relaxing accommodation of an eye. As described in the Cornsweet patent, relaxation of accommodation may be produced by presenting a defocused flashing light source to an eye through a pin-hole aperture positioned a selected distance from the eye's lens. Trachtman U.S. Pat. Nos. 4,533,221 and 4,660,945, also incorporated herein in their entireties by this reference, discuss other techniques for performing accommodation training.

Among the equipment frequently used by practitioners for eye examinations is the optical slit lamp. Commercially available slit lamps usually include a Galilean binocular microscope connected to optional accessories such as photographic systems (if, e.g., retinal photography is to be performed or recorded measurements are desired), Pachometers (for measuring corneal thickness), or Goldmann applanation tonometers (for assessing eyeball tension). Such slit lamps also may be integrated with laser transmission or other systems for performing ophthalmic surgery or used by neurologists in evaluating, for example, ocular muscle paralysis or the existence of ocular tumors.

One commercial slit lamp, the Topcon Photo Slit Lamp SL-5D available from the Topcon Instrument Company of America, 65 West Century Road, Paramus, N.J. 07652, includes an annular fixation wand or target having a luminous fiber optic tip. The target is connected to the end of an extendable arm and may be positioned by the practitioner near a patient's eyes to attract the patient's attention. The patient is directed to focus both eyes—including the subject eye—on the illuminated target, thereby positioning the subject eye as necessary to perform the optical examination or procedure.

During the examination the practitioner may reposition the subject eye simply by moving the illuminated target. Repositioning the target, however, typically requires that the practitioner interrupt the examination, peer away from the binocular microscope to the extendable arm, and physically adjust the arm until the target is appropriately located. Because trial-and-error techniques must be used to reposition the target, time consuming delays often exist when frequent repositioning occurs. Moreover, accommodation and convergence result when the patient attempts to focus on the nearby target, causing ocular muscle strain and fatigue strain and their consequent examination-related problems.

SUMMARY OF THE INVENTION

The present invention provides means for relaxing accommodation of an eye undergoing examination or other optical or medical procedures while concurrently permitting and facilitating positioning of the subject eye. The invention includes a patch, cover, or other device designed to occlude from ambient light and visually stimulate the eye opposite the subject eye. The interior of the patch facing the occluded eye includes a set or array of light sources, such as LEDs or LCD pixels, illumination of which is controlled electrically by the practitioner.

To position the subject eye, the practitioner illuminates a selected one (or ones) of the light sources within the patch and asks the patient to fixate on the source. As the occluded eye moves to fixate on the illuminated source, the subject eye will follow the movement, thereby repositioning itself. Because the eye opposite the subject eye is occluded, the image seen by it appears to the brain to be at infinity rather than nearby, causing the ocular muscles of both eyes to relax. Using an array of light sources allows the practitioner to reposition the illuminated source relative to the eye without physically moving a wand or otherwise engaging in trial-and-error techniques requiring interruption of the examination or procedure and consequent loss of concentration.

It is therefore an object of the present invention to provide means for relaxing accommodation of an eye undergoing examination or other optical or medical procedures.

It is another object of the present invention to provide means for permitting and facilitating positioning of the subject eye.

It is a further object of the present invention to provide means for relaxing accommodation of a subject eye by occluding and visually stimulating the eye opposite the subject eye.

It is an additional object of the present invention to provide means for permitting the practitioner to direct movement of the subject eye without physically moving a wand or otherwise resorting to trial-and-error techniques.

Other objects, features, and advantages of the present invention will become apparent with reference to the remainder of the written portion and the drawings of this application.

BRIEF DESCRIPTION OF THE DRAWINGS

FIG. 3 is a perspective view of a second alternate embodiment of the present invention designed to be worn about the head of a patient.

FIG. 4 is a perspective view of a third alternate embodiment of the present invention designed to be held by the patient, practitioner, or other suitable individual or apparatus.

FIG. 5 is a plan view of the interior of the embodiments of FIGS. 1-4 of the present invention detailing the illumination set or array.

DETAILED DESCRIPTION

Figure 1:
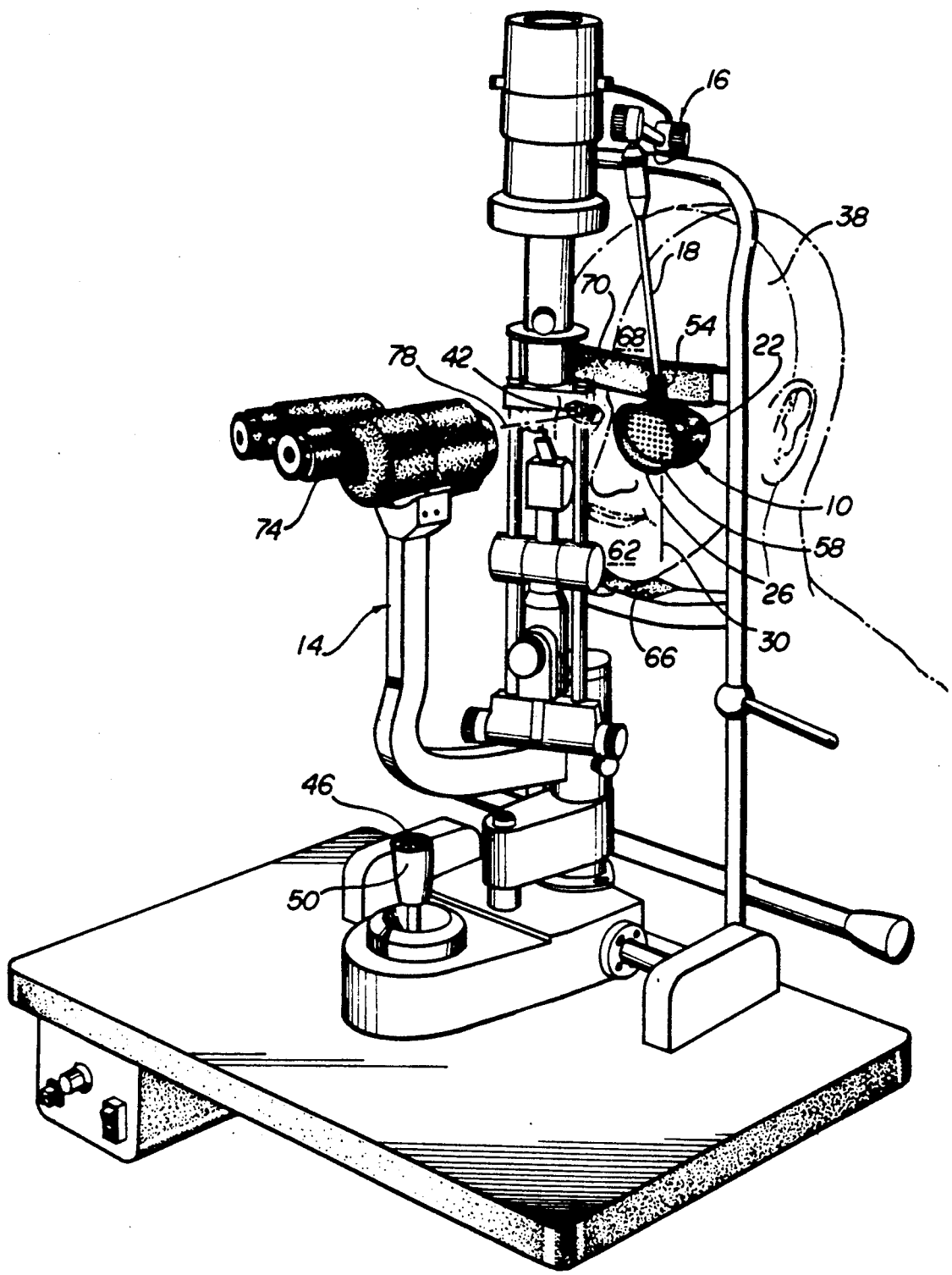
FIG. 1 is a perspective view of an embodiment of the present invention shown connected to a slit lamp.

FIG. 1 illustrates a first embodiment of the device 10 of the present invention connected to slit lamp 14 by extendable arm assembly 16 and conduit 18. Device 10 includes dual eye pieces 22 and 26 formed about an axis 30 defined by conduit 18. Eye piece 22 is adapted to follow the approximate facial contours surrounding the left eye 34 (FIG. 2) of a patient 38, while eye piece 26 is similarly adapted for the patient's right eye 42. Conduit 18 and extendable arm assembly 16 house wires electrically connecting device 10 to a suitable control mechanism, such as switch set 46 positioned atop joystick 50 of slit lamp 14, and a power supply. Slit lamp 14 may be any existing lamp adapted to accommodate device 10 of the present invention. As noted earlier, at least one such slit lamp 14 is available from the Topcon instrument Company of America.

Also shown in FIG. 1 is swivel mount 54, which permits device 10 to rotate about axis 30. Rotating device 10 allows the practitioner (or other individual, including patient 38) to position eye pieces 22 and 26 as appropriate before the left (34) and right (42) eyes, respectively, of patient 38. Extendable arm assembly 16 similarly allows conduit 18 to move relative to slit lamp 14 and patient 38, permitting adjustment of the positions of eye pieces 22 and 26 as desired to conform them to facial characteristics of particular patients 38.

Each of eye pieces 22 and 26 includes multiple light sources 58 (shown in FIG. 1 for eye piece 26; see also FIG. 5) used for visually stimulating and facilitating repositioning of eyes 34 and 42. Illumination of any one (or more) of the light sources 58 is electrically controllable by the practitioner using switch set 46. Light sources 58 may be LEDS, LCD pixels, fiber optics, incandescent or fluorescent light-emitting sources, or any other suitable means for providing light at frequencies in the visible spectrum. Depending on the type of light sources 58 selected and the functions to be performed by device 10, additional electric circuitry may be connected to the device 10 as necessary to, for example, drive light sources 58, serve as an interface with other electric or electronic components such as (but not limited to) a computer or video camera, or provide means for the practitioner to monitor the status of each light source 58 during the examination or procedure. Additional circuitry also could couple light sources 58 to, for example, medical lasers or other equipment, to facilitate alignment of such equipment with the patient's line-of-sight.

Operation of device 10 is straightforward and will be explained with reference to left eye 34. For purposes of this explanation, therefore, right eye 42 is the "subject" eye undergoing examination or other such optical or medical procedure. However, those having ordinary skill in the art will recognize that device 10 may be utilized in connection with examination or other procedures involving left eye 34 merely by moving the device 10 to the opposite (right (42)) eye and rotating it about axis 30 as discussed above.

Initially, patient 38 is instructed to sit with his or her chin 62 resting on support 66 and his or her forehead 68 against bar 70 of slit lamp 14. Device 10 then is positioned (by, for example, the practitioner or patient 38) so that eye piece 22 contacts the facial area of patient 38 surrounding left eye 34. If properly located, eye piece 22 will occlude left eye 34 from ambient light; right eye 38, in contrast, is not obstructed by device 10 and remains available for examination or other optical or medical procedures. Because right eye 38 is unobstructed, the practitioner may use, for example, binocular microscopes 74 (as shown in FIG. 1) or other equipment for examination.

To obtain a nominal, or reference line-of-sight 78 for the right eye 42 of patient 38, the practitioner need merely illuminate light source 58A (FIG. 5) in the center of eye piece 22 and instruct patient 38 to view source 58A. As left eye 34 moves in an effort to view light source 58A within eye piece 22, right eye 42 will follow the movement, with its eventual stopping point determining reference line-of-sight 78. Should the practitioner subsequently desire to examine right eye 42 while positioned along other than line-of-sight 78, he or she need merely illuminate an appropriate light source 58 other than central source 58A and instruct patient 38 to view the newly-illuminated source 58. Again, as patient 38 repositions occluded left eye 34 to view the newly-illuminated source 58, right eye 42 too will be repositioned correspondingly as it follows the movement. Those skilled in the art will recognize that having a set or array of light sources 58 within eye piece 22 permits left and right eyes 34 and 42 to site along numerous, indeed virtually infinite, lines other than reference line-of-sight 78. Persons skilled in the art will similarly recognize that the practitioner need not establish a reference line-of-sight 78, but may direct right eye 42 to be positioned and conduct the examination or procedure in any suitable manner.

Because left eye 34 is occluded from ambient light, the retinal image caused by the luminous light source 58 remains blurry and the brain of patient 38 does not sense the light source 58 as being nearby. As a result, no convergence, or "awareness of nearness," is stimulated.

Instead, patient 38 perceives the illumination as being at an infinite distance. This perception of having vision directed at infinity causes the fibers of the ciliary muscles of patient 38 to relax, decreasing accommodation and its consequent ocular muscle fatigue.

Avoiding ocular muscle fatigue typically increases the comfort of patient 38, making examinations and other procedures more pleasant for both the patient 38 and the practitioner. Relaxing eyes 34 and 42 also decreases the likelihood that patient 38 will attempt to reposition right eye 42 or allow it to wander during the procedure, thereby minimizing errors associated with undesired movement of the subject eye. Maintaining constant position of right eye 42 is especially important during certain procedures, such as laser surgery, which otherwise might damage healthy ocular tissue, and during procedures such as-retinal photography requiring precise positioning of the subject eye over relatively long periods of time. Preventing accommodation and convergence also decreases measurement corruption during examinations, potentially increasing the accuracy of eyeglass lens prescriptions. The present invention may be used for a variety of other purposes as well, including (but not limited to) evaluating eye tracking ability in infants and low vision patients, detecting ocular muscle weakness, paralysis, and other problems (such as those causing "crossed eyes" or caused by brain tumors, trauma, or otherwise, some of which might require surgery), and helping maintain an eye in position while a foreign object is removed.

Figure 2:
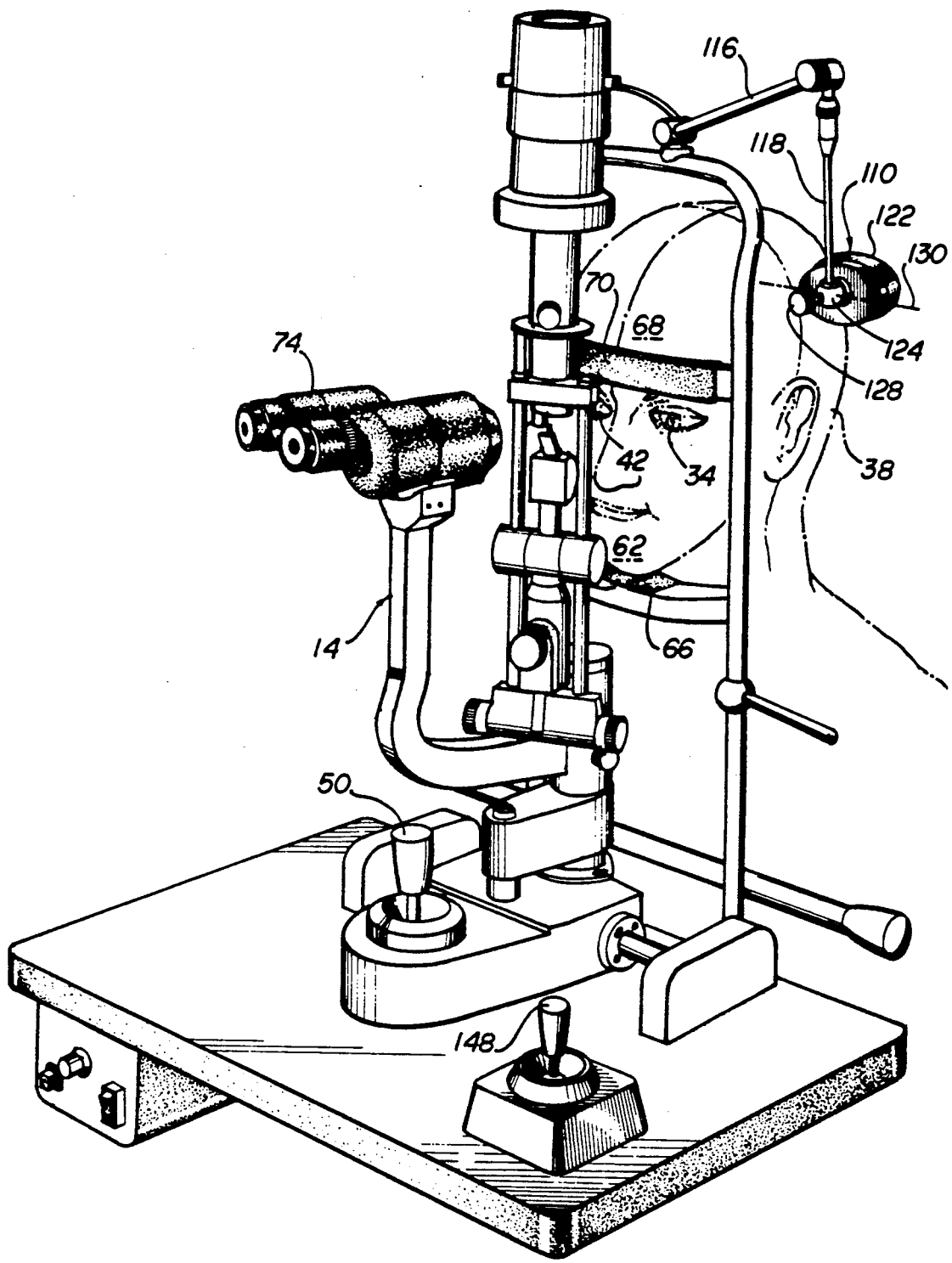
FIG. 2 is a perspective view of a first alternate embodiment of the present invention also shown connected to a slit lamp.

FIG. 2 illustrates an alternate device 110 of the present invention having a single eye piece 122. As shown in FIG. 2, device 110 may be connected to the extendable arm assembly 116 and conduit 118 of various existing slit lamps 114 and replace the annular fixation wand or other target presently in use. Eye piece 122 of device 110 may be coupled to conduit 118 via a ball joint 124 (or any other suitable mechanism), permitting the eye piece 122 to rotate about axis 130. Because facial contours surrounding the eyes of most patients are approximately symmetrical, eye piece 122, if fitted to one of left and right eyes 34 and 42, need merely be rotated 180° about axis 130 to adapt it for use with the other eye. Alternatively, eye piece 122 (and, for that matter, eyepiece 22) may be designed for use with both eyes 34 and 42 without rotation. Also shown in FIG. 2 is threaded member 128, which may be tightened to secure the position of eye piece 122 once fitted to an eye 34 or 42.

Device 110, like device 10 of FIG. 1, includes multiple light sources 58 (FIG. 5) for facilitating repositioning of the occluded, and thereby subject, eyes during examination or other optical or medical procedures. Once positioned before the nonsubject eye, therefore, operation of device 110 is essentially the same as for device 10. FIG. 2 also illustrates a joystick 148 for controlling illumination of light sources 58 as one of many alternatives to switch set 46.

Additional alternate devices 210 and 310 of the present invention are detailed, respectively, in FIGS. 3-4. FIG. 3 illustrates device 210 attached to a band 212 for wearing about the head of patient 38. Band 212 includes hook and loop fasteners 216 or other suitable means for securing device 210 about the patient's head. Device 210 includes an eye piece 222 having bellows 228 for adjusting to the facial contours surrounding both the left and right eyes 34 and 42 of patient 38. Device 210 also includes light sources 58 (FIG. 5) within eye piece 212 and a second set of light sources 258 designed to be visible to the practitioner when device 210 is in use. Sources 258, which correspond to sources 58 in a one-to-one relationship, provide the practitioner with visible confirmation of the particular source or sources 58 which are illuminated at any given time. Of course, any other suitable means for confirming which sources 58 are illuminated may be employed as alternatives to light sources 258.

Device 310 represents a hand-held version of the present invention. Conduit 318 connects dual eye pieces 322 and 326 to handle 330, with electrical connections occurring at control 344. As illustrated in FIGS. 3-4, control 344 includes switch set 346 for illuminating selected one or ones of light sources 58. Also shown as forming control 344 are battery compartment 348, variable resistor/switch 352, and input jack 356. Switch 352 may be used to vary the intensity of the illumination emanating from sources 58, while jack 356 permits a foot-operated switch or other suitable device to be connected to control 344 for hands-free operation. Control 344 alternatively or additionally could be, e.g., voice activated.

An array of light sources 58 usable with devices 10, 110, 210, 310, and 410 is shown in the eyepiece 522 of FIG. 5. Because eyepiece 522 is designed to occlude a patient's eye from ambient light, it includes an opaque wall or backing 526 behind sources 58. Of course, arrays other than that shown in FIG. 5 may be used in accordance with the present invention; in fact, any such array or set of sources 58 may be used so long as it permits directing movement of a patient's eye.

The foregoing is provided for purposes of illustration, explanation, and description of embodiments of the present invention. Modifications and adaptations to these embodiments, including interchangeability among the embodiments of various features described herein, will be apparent to those of ordinary skill in the art and may be made without departing from the scope or spirit of the invention. The second set of light sources 258, for example, could be hingedly-mounted to the exterior of eyepiece 212 to permit the practitioner to confirm the illumination status of light sources 58 from varying positions relative to patient 38. The second set of light sources 258 also need not be physically positioned on eyepiece 212, but could be, e.g., positionable near the subject eye so as to permit the practitioner to determine or confirm that the subject eye is, in fact, suitably following the intended movement of the occluded eye. Furthermore, as appropriately modified the devices of the present invention could be used in connection with the lens-marking devices described in application Ser. Nos. 07/642,299 and 07/467,269, permitting repositioning of the eye and subsequent marking of a lens using a single device.

I claim:

1. An apparatus for use in positioning a first eye of a patient having (i) first and second eyes, which first eye is capable of following movement of the second eye, and (ii) a facial region surrounding the second eye, comprising:

a. means for (i) contacting the facial region surrounding the second eye and (ii) occluding the second eye, but not the first eye, from ambient light; and b. means, comprising a plurality of selectively illuminable light sources contained within the occluding means, for providing alternate fixation targets for the second eye to permit relative movement of the second eye and any selected one of the selectively illuminable light sources when the apparatus is in use.

2. An apparatus according to claim 1 further comprising means for mounting the occluding means to a slit lamp.

3. An apparatus according to claim 2 in which the mounting means comprises means for adjusting the occluding means relative to the first and second eyes of the patient.

4. An apparatus according to claim 2 further comprising a plurality of light sources, corresponding on a one-to-one basis with the plurality of selectively illuminable light sources, for providing confirmation of the illumination status of the selectively illuminable light sources.

5. An apparatus according to claim 1 in which the patient has a head and further comprising means for attaching the occluding means about the patient's head.

6. An apparatus according to claim 5 in which the mounting means further comprises an extendable arm connecting the slit lamp and the occluding means.

7. An apparatus according to claim 1 further comprising a handle, connected to the occluding means, for permitting hand-held operation of the apparatus.

8. An apparatus for use in positioning a first eye of a patient having first and second eyes, which first eye is capable of following movement of the second eye, comprising:
   a. means for occluding the second eye, but not the first eye, from ambient light;
   b. means, comprising a plurality of selectively illuminable light sources contained within the occluding means, for prompting movement of the second eye relative to the occluding means responsive to illumination of a selected light source; and
   c. a plurality of light sources, corresponding on a one-to-one basis with the plurality of selectively illuminable light sources, for providing confirmation of the illumination status of the selectively illuminable light sources.

9. An apparatus for performing optical procedures on a patient having two eyes and a face, comprising:
   a. a slit lamp;
   b. means for occluding one eye from ambient light, comprising:
      i. an eyepiece; and
      ii. means for adjusting the eyepiece to conform to the facial contours of the patient;
   c. a first array of light sources, selectively-illuminable and contained within the eyepiece, for providing alternate fixation targets for the second eye;
   d. a second array of light sources, visible from locations external to the eyepiece and which corresponds to the first array, for visually confirming the illumination status of the light sources of the first array contained within the eyepiece; and
   e. means for connecting the occluding means to the slit lamp.

10. An apparatus according to claim 9 in which the connecting means comprises:
    a. an extendable arm connected to the slit lamp; and
    b. means, interposed between the extendable arm and the occluding means, for permitting adjustment of the occluding means relative to the patient's face.

11. A method for positioning and relaxing accommodation of a first eye of a patient having first and second eyes, which first eye is capable of following movement of the second eye, comprising the steps of:
    a. occluding the second eye, but not the first eye, from ambient light using occluding means;
    b. providing a target for the second eye by illuminating at least one of a plurality of selectively illuminable light sources contained within the occluding means; and
    c. directing the patient to move the second eye relative to the occluding means to fixate on the target.

12. A method according to claim 11 further comprising the step of performing an optical procedure on the first eye resulting from movement of the second eye in response to the direction to the patient.

13. A method for positioning and relaxing accommodation of a first eye of a patient having a brain, first and second eyes, and first and second ocular muscles corresponding, respectively, to the first and second eyes, which first eye is capable of following movement of the second eye, comprising the steps of:
    a. occluding the second eye, but not the first eye, from ambient light using occluding means;
    b. providing a target for the second eye by illuminating at least one of a plurality of selectively illuminable light sources contained within the occluding means; and
    c. directing the patient to move the second eye relative to the occluding means in an attempt to view the target, thereby:
       i. causing the patient to move the second eye in an attempt to view the target;
       ii. causing the first eye to move to follow the second eye;
       iii. causing the brain to perceive the target as being at an approximately infinite distance from the second eye; and
       iv. causing the first and second ocular muscles to relax.

* * * * *